United States Patent [19]

Shoop et al.

[11] Patent Number: 5,595,991
[45] Date of Patent: Jan. 21, 1997

[54] ANTHELMINTIC USE OF NODULISPORIC ACID AND ANALOGS THEREOF

[75] Inventors: Wesley Shoop, Somerville; Dan A. Ostlind, Watchung; Bruce F. Michael, Whitehouse Station, all of N.J.

[73] Assignee: Merck & Co., Inc., Rahway, N.J.

[21] Appl. No.: 406,447

[22] Filed: Mar. 20, 1995

[51] Int. Cl.⁶ .......................... A61K 31/40; A61K 31/44; A61K 31/445; A61K 31/535
[52] U.S. Cl. ..................... 514/233.2; 514/323; 514/339; 514/410
[58] Field of Search ................... 514/410, 233.2, 514/323, 339

[56] References Cited

U.S. PATENT DOCUMENTS 5,339,582  3/1995  Dombrowski .................. 514/410

Primary Examiner—Phyllis G. Spivack
Attorney, Agent, or Firm—Mollie M. Yang; David L. Rose

[57] ABSTRACT

The present invention provides a method for the treatment of helminthiasis which comprises administering to an infected host an effective amount of nodulisporic acid or a analog thereof.

3 Claims, No Drawings

ANTHELMINTIC USE OF NODULISPORIC ACID AND ANALOGS THEREOF

BACKGROUND OF THE INVENTION

Nodulosporic acid and two related components are antiparasitic agents and ectoparasiticidal agents isolated from the fermentation culture of Nodulisporium sp. MF-5954 (ATCC 74245). These three compounds have the following structures:

nodulisporic acid (compound A)

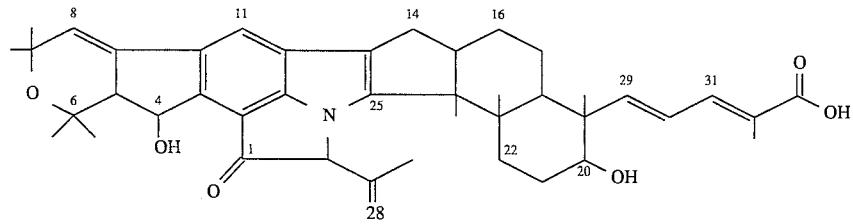

29,30-dihydro-20,30-oxa-nodulisporic acid (compound B)

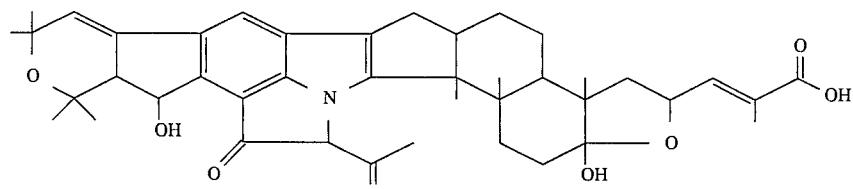

31-hydroxy-20,30-oxa-29,30,31,32-tetrahydro-nodulisporic acid (compound C)

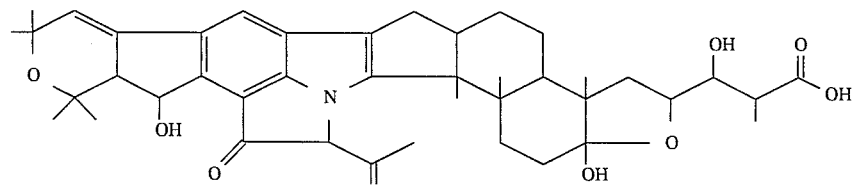

SUMMARY OF THE INVENTION

This invention relates to new acaricidal, antiparasitic, insecticidal and anthelmintic agents related to the nodulisporic acids, to processes for their preparation, compositions thereof, their use in the treatment of parasitic infections in human and animals, and their use in the treatment of parasitic infections in plants or plant products. The present invention further provides a method for the treatment of helminthiasis in human and animals using the natural nodulisporic acids (Compounds A, B and C), and nodulisporic acids analogs of the present invention.

DETAILED DESCRIPTION OF THE INVENTION

The present invention provides compounds of formula I:

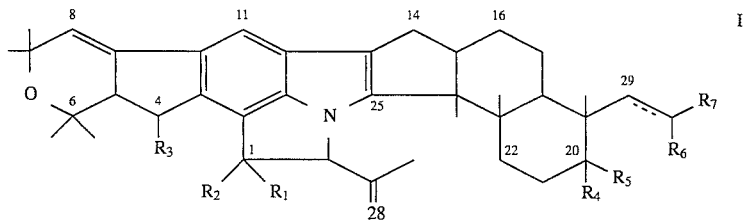

wherein
$R_1$ is
  (1) hydrogen,
  (2) optionally substituted $C_1$–$C_{10}$ alkyl, (3) optionally substituted $C_2-C_{10}$ alkenyl,
(4) optionally substituted $C_2-C_{10}$ alkynyl,
(5) optionally substituted $C_3-C_8$ cycloalkyl,
(6) optionally substituted $C_5-C_8$ cycloalkenyl where the substitutents on the alkyl, alkenyl, alkynyl, cycloalkyl and cycloalkenyl are 1 to 3 groups independently selected from $C_1-C_5$ alkyl, $C_1-C_{10}$ alkoxy, $C_1-C_{10}$ alkylthio, $C_1-C_{10}$ alkylsulfonyl, $C_3-C_8$ cycloalkyl, hydroxy, halogen, cyano, carboxy, amino, $C_1-C_{10}$ monoalkylamino, $C_1-C_{10}$ dialkylamino, $C_1-C_{10}$ alkanoyl amino and aroyl amino wherein said aroyl is optionally substituted with 1 to 3 groups independently selected from $C_1-C_4$ alkyl, $C_1-C_4$ alkoxy, $C_1-C_4$ alkylthio, $C_2-C_4$ alkenyl, $C_2-C_4$ alkynyl, $C_1-C_3$-perfluoroalkyl, amino, hydroxy, halogen, $C_1-C_5$ monoalkylamino, $C_1-C_5$ dialkylamino and $C_1-C_5$ alkanoyl amino, (7) aryl $C_0-C_5$ alkyl wherein said aryl is optionally substituted with 1 to 3 groups independently selected from $C_1-C_4$ alkyl, $C_1-C_4$ alkoxy, $C_1-C_4$ alkylthio, $C_2-C_4$ alkenyl, $C_2-C_4$ alkynyl, $C_1-C_3$-perfluoroalkyl, amino, hydroxy, carboxy, halogen, $C_1-C_5$ monoalkylamino, $C_1-C_5$ dialkylamino and $C_1-C_5$ alkanoyl amino, (8) $C_1-C_5$ perfluoroalkyl (9) a 5- or 6-membered ring containing from 1 to 4 heteroatoms independently selected from oxygen, sulfur and nitrogen atoms optionally substituted by 1 to 3 groups independently selected from hydroxy, oxo, $C_1-C_{10}$ alkyl and halogen, and which may be saturated or partly unsaturated, $R_2$, $R_3$, and $R_4$ are independently $OR^a$, $OCO_2R^b$, $OC(O)NR^cR^d$; or $R_1+R_2$ represent $=O$, $=NOR^a$ or $=N-NR^cR^d$;

$R_5$ and $R_6$ are H; or $R_5$ and $R_6$ together represent —O—;

$R_7$ is
(1) CHO, or
(2) the fragment

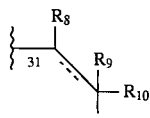

$R_8$ is independently
(1) H, or
(2) $OR^a$;
(3) $NR^cR^d$ $R_9$ is independently
(1) H, or
(2) $OR^a$;

$R_{10}$ is
(1) CN,
(2) $C(O)OR^b$,
(3) $C(O)N(OR^b)R^c$,
(4) $C(O)NR^cR^d$,
(5) $NHC(O)OR^b$,
(6) $NHC(O)NR^cR^d$,
(7) $CH_2OR^a$,
(8) $CH_2OCO_2R^b$, or
(9) $CH_2OC(O)NR^cR^d$;

=== represents a single or a double bond;

$R^a$ is
(1) hydrogen,
(2) optionally substituted $C_1-C_{10}$ alkyl,
(3) optionally substituted $C_3-C_{10}$ alkenyl,
(4) optionally substituted $C_3-C_{10}$ alkynyl,
(5) optionally substituted $C_1-C_{10}$ alkanoyl,
(6) optionally substituted $C_3-C_{10}$ alkenoyl,
(7) optionally substituted $C_3-C_{10}$ alkynoyl,
(8) optionally substituted aroyl,
(9) optionally substituted aryl,
(10) optionally substituted $C_3-C_7$ cycloalkanoyl,
(11) optionally substituted $C_4-C_7$ cycloalkenoyl,
(12) optionally substituted $C_1-C_{10}$ alkylsulfonyl
(13) optionally substituted $C_3-C_8$ cycloalkyl
(14) optionally substituted $C_5-C_8$ cycloalkenyl where the substitutents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 5 groups independently selected from hydroxy, $C_1-C_6$ alkoxy, $C_3-C_7$ cycloalkyl, aryl $C_1-C_3$ alkoxy, $NR^gR^h$, $CO_2R^b$, $CONR^cR^d$ and halogen,

(15) $C_1-C_5$ perfluoroalkyl,

(16) arylsulfonyl optionally substituted with 1 to 3 groups independently selected from $C_1-C_5$ alkyl, $C_1-C_5$ perfluoroalkyl, nitro, halogen or cyano,

(17) a 5- or 6-membered ring containing 1 to 4 heteroatoms selected from oxygen, sulfur and nitrogen optionally substituted by 1 to 4 groups independently selected from $C_1-C_5$ alkyl, $C_1-C_5$ alkenyl, $C_1-C_5$ perfluoroalkyl, amino, $C(O)R^cR^d$, cyano, $CO_2R^b$ or halogen, and which may be saturated or partly unsaturated;

$R^b$ is
(1) H,
(2) optionally substituted aryl,
(3) optionally substituted $C_1-C_{10}$ alkyl,
(4) optionally substituted $C_3-C_{10}$ alkenyl, or
(5) optionally substituted $C_3-C_{10}$ alkynyl, where the substituents on the aryl, alkyl, alkenyl or alkynyl are from 1 to 5 groups independently selected from hydroxy, $C_1-C_6$ alkoxy, $C_3-C_7$ cycloalkyl, halogen, $C_1-C_5$ alkanoyloxy, $C(O)NR^cR^d$, $CO_2R^b$, formyl, —$NR^gR^h$, optionally substituted aryl, and optionally substituted aryl $C_1-C_3$ alkoxy, wherein the aryl substituents are 1 to 3 groups independently selected from $R^e$;

$R^c$ and $R^d$ are independently $R^b$; or $R^c$ and $R^d$ together with the N to which they are attached form a 3- to 7-membered ring containing 0 to 2 additional heteroatoms selected from O, $S(O)_m$, and N, optionally substituted with 1 to 3 groups independently selected from $R^g$ and oxo;

$R^e$ is
(1) halogen,
(2) $C_1-C_7$ alkyl,
(3) $C_1-C_3$ perfluoroalkyl,
(4) —$S(O)_mR^i$,
(5) cyano,
(6) nitro,
(7) $R^jO(CH_2)_v$—,
(8) $R^jCO_2(CH_2)_v$—,
(9) $R^jOCO(CH_2)_v$,
(10) optionally substituted aryl where the substituents are from 1 to 3 of halogen, $C_1-C_6$ alkyl, $C_1-C_6$ alkoxy, or hydroxy;

v is 0 to 3;

$R^g$ and $R^h$ are independently (1) hydrogen,
(2) $C_1$–$C_6$ alkyl,
(3) aryl,
(4) aryl $C_1$–$C_6$ alkyl,
(5) $C_1$–$C_5$ alkoxycarbonyl,
(6) $C_1$–$C_5$ alkylcarbonyl, or
(7) $C_1$–$C_5$ alkanoyl $C_1$–$C_6$ alkyl; or $R^g$ and $R^h$ together with the N to which they are attached form a 3- to 7-membered ring containing 0 to 2 additional heteroatoms selected from O, $S(O)_m$, and N, optionally substituted with 1 to 3 groups independently selected from $R^g$ and oxo;

$R^i$ and $R^j$ are independently
(1) hydrogen,
(2) $C_1$–$C_3$ perfluoroalkyl,
(3) optionally substituted $C_1$–$C_6$ alkyl, where the substituents are aryl or substituted aryl;
(4) aryl or substituted aryl where the aryl substituents are from 1 to 3 groups independently selected from halogen, $C_1$–$C_6$ alkyl, $C_1$–$C_6$ alkoxy, or hydroxy;

m is 0 to 2; and excluding nodulisporic acid, 29,30-dihydro-20,30-oxanodulisporic acid, and 31-hydroxy-20,30-oxa-29,30, 31,32-tetrahydronodulisporic acid; or a pharmaceutically acceptable salt thereof.

Preferred embodiment of the present invention are realized in formul I wherein $R^1$ is
(1) hydrogen,
(2) optionally substituted $C_1$–$C_7$ alkyl,
(3) optionally substituted $C_2$–$C_7$ alkenyl,
(4) optionally substituted $C_2$–$C_7$ alkynyl,
(5) optionally substituted $C_5$–$C_6$ cycloalkyl,
(6) optionally substituted $C_5$–$C_6$ cycloalkenyl where the substitutents on the alkyl, alkenyl, alkynyl, cycloalkyl and cycloalkenyl are 1 to 3 groups independently selected from $C_1$–$C_3$ alkyl, $C_1$–$C_7$ alkoxy, $C_1$–$C_7$ alkylthio, $C_1$–$C_7$ alkylsulfonyl, $C_5$–$C_6$ cycloalkyl, hydroxy, halogen, cyano, carboxy, amino, $C_1$–$C_7$ monoalkylamino, $C_1$–$C_7$ dialkylamino, $C_1$–$C_7$ alkanoyl amino and aroyl amino wherein said aroyl is optionally substituted with 1 to 3 groups independently selected from $C_1$–$C_3$ alkyl, $C_1$–$C_3$ alkoxy, $C_1$–$C_3$ alkylthio, $C_2$–$C_3$ alkenyl, $C_2$–$C_3$ alkynyl, $C_1$–$C_3$-perfluoroalkyl, amino, hydroxy, halogen, $C_1$–$C_3$ monoalkylamino, $C_1$–$C_3$ dialkylamino and $C_1$–$C_3$ alkanoyl amino, (7) aryl $C_0$–$C_3$ alkyl wherein said aryl is optionally substituted with 1 to 3 groups independently selected from $C_1$–$C_3$ alkyl, $C_1$–$C_3$ alkoxy, $C_1$–$C_3$ alkylthio, $C_2$–$C_3$ alkenyl, $C_2$–$C_3$ alkynyl, $C_1$–$C_3$-perfluoroalkyl, amino, hydroxy, carboxy, halogen, $C_1$–$C_3$ monoalkylamino, $C_1$–$C_3$ dialkylamino and $C_1$–$C_3$ alkanoyl amino, (8) $C_1$–$C_3$ perfluoroalkyl
(9) a 5- or 6-membered ring containing from 1 to 4 heteroatoms independently selected from oxygen, sulfur and nitrogen atoms optionally substituted by 1 to 3 groups independently selected from hydroxy, oxo, $C_1$–$C_5$ alkyl and halogen, and which may be saturated or partly unsaturated, $R^a$ is
(1) hydrogen,
(2) optionally substituted $C_1$–$C_7$ alkyl,
(3) optionally substituted $C_3$–$C_7$ alkenyl,
(4) optionally substituted $C_3$–$C_7$ alkynyl,
(5) optionally substituted $C_1$–$C_7$ alkanoyl,
(6) optionally substituted $C_3$–$C_7$ alkenoyl,
(7) optionally substituted $C_3$–$C_7$ alkynoyl,
(8) optionally substituted aroyl,
(9) optionally substituted aryl,
(10) optionally substituted $C_5$–$C_6$ cycloalkanoyl,
(11) optionally substituted $C_5$–$C_6$ cycloalkenoyl,
(12) optionally substituted $C_1$–$C_7$ alkylsulfonyl
(13) optionally substituted $C_5$–$C_6$ cycloalkyl
(14) optionally substituted $C_5$–$C_6$ cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 5 groups independently selected from hydroxy, $C_1$–$C_6$ alkoxy, $C_5$–$C_6$ cycloalkyl, aryl $C_1$–$C_3$ alkoxy, $NR^gR^h$, $CO_2R^b$, $CONR^cR^d$ and halogen,

(15) $C_1$–$C_3$ perfluoroalkyl,
(16) arylsulfonyl optionally substituted with 1 to 3 groups independently selected from $C_1$–$C_3$ alkyl, $C_1$–$C_3$ perfluoroalkyl, nitro, halogen or cyano,
(17) a 5- or 6-membered ring containing 1 to 4 heteroatoms selected from oxygen, sulfur and nitrogen optionally substituted by 1 to 4 groups independently selected from $C_1$–$C_3$ alkyl, $C_1$–$C_3$ alkenyl, $C_1$–$C_3$ perfluoroalkyl, amino, $C(O)R^cR^d$, cyano, $CO_2R^b$ or halogen, and which may be saturated or partly unsaturated;

$R^b$ is
(1) H,
(2) optionally substituted aryl,
(3) optionally substituted $C_1$–$C_7$ alkyl,
(4) optionally substituted $C_3$–$C_7$ alkenyl, or
(5) optionally substituted $C_3$–$C_7$ alkynyl, where the substituents on the aryl, alkyl, alkenyl or alkynyl are from 1 to 5 groups independently selected from hydroxy, $C_1$–$C_3$ alkoxy, $C_5$–$C_6$ cycloalkyl, halogen, $C_1$–$C_3$ alkanoyloxy, $C(O)NR^cR^d$, $CO_2R^b$, formyl, $—NR^gR^h$, optionally substituted aryl, and optionally substituted aryl $C_1$–$C_3$ alkoxy, wherein the aryl substituents are 1 to 3 groups independently selected from $R^e$;

$R^e$ is
(1) halogen,
(2) $C_1$–$C_3$ alkyl,
(3) $C_1$–$C_3$ perfluoroalkyl,
(4) $—S(O)_mR^i$,
(5) cyano,
(6) nitro,
(7) $R^jO(CH_2)_v—$,
(8) $R^jCO_2(CH_2)_v—$,
(9) $R^jOCO(CH_2)_v$,
(10) optionally substituted aryl where the substituents are from 1 to 3 of halogen, $C_1$–$C_3$ alkyl, $C_1$–$C_3$ alkoxy, or hydroxy;

$R^g$ and $R^h$ are independently
(1) hydrogen,
(2) $C_1$–$C_5$ alkyl,
(3) aryl,
(4) aryl $C_1$–$C_4$ alkyl,
(5) $C_1$–$C_4$ alkoxycarbonyl,
(6) $C_1$–$C_4$ alkylcarbonyl, or
(7) $C_1$–$C_4$ alkanoyl $C_1$–$C_5$ alkyl; or $R^g$ and $R^h$ together with the N to which they are attached form a 5- to 6-membered ring containing 0 to 2 additional heteroatoms selected from O, $S(O)_m$, and N, optionally substituted with 1 to 3 groups independently selected from $R^g$ and oxo;

$R^i$ and $R^j$ are independently
  (1) hydrogen,
  (2) $C_1$–$C_3$ perfluoroalkyl,
  (3) optionally substituted $C_1$–$C_3$ alkyl, where the substituents are aryl or substituted aryl;
  (4) aryl or substituted aryl where the aryl substituents are from 1 to 3 groups independently selected from halogen, $C_1$–$C_3$ alkyl, $C_1$–$C_3$ alkoxy, or hydroxy; and all other groups are as defined under formula I.

More preferred embodiment of the present invention is realized in formula I wherein $R_1$ is
  (1) hydrogen,
  (2) optionally substituted $C_1$–$C_5$ alkyl,
  (3) optionally substituted $C_2$–$C_5$ alkenyl,
  (4) optionally substituted $C_2$–$C_5$ alkynyl,
  (5) optionally substituted $C_5$–$C_6$ cycloalkyl,
  (6) optionally substituted $C_5$–$C_6$ cycloalkenyl where the substitutents on the alkyl, alkenyl, alkynyl, cycloalkyl and cycloalkenyl are 1 to 3 groups independently selected from $C_1$–$C_3$ alkyl, $C_1$–$C_5$ alkoxy, $C_1$–$C_5$ alkylthio, $C_1$–$C_5$ alkylsulfonyl, $C_5$–$C_6$ cycloalkyl, hydroxy, halogen, cyano, carboxy, amino, $C_1$–$C_5$ monoalkylamino, $C_1$–$C_5$ dialkylamino, $C_1$–$C_5$ alkanoyl amino and aroyl amino wherein said aroyl is optionally substituted with 1 to 3 groups independently selected from methyl, methoxy, methylthio, trifluoromethyl, amino, hydroxy, halogen, methylamino, dimethalkylamino and acetylamino, (7) aryl $C_0$–$C_1$ alkyl wherein said aryl is optionally substituted with 1 to 3 groups independently selected from methyl, methoxy, methylthio, trifluoromethyl, amino, hydroxy, carboxy, halogen, methylamino, dimethylamino and acetylamino, and where said aryl is selected from phenyl, thiazolyl, oxazolyl, pyridyl, imidazolyl, thiophenyl and furanyl,
  (8) trifluoromethyl
  (9) a 5- or 6-membered ring containing from 1 to 4 heteroatoms independently selected from oxygen, sulfur and nitrogen atoms optionally substituted by 1 to 3 groups independently selected from hydroxy, oxo, $C_1$–$C_3$ alkyl and halogen, and which may be saturated or partly unsaturated, $R^a$ is
  (1) hydrogen,
  (2) optionally substituted $C_1$–$C_5$ alkyl,
  (3) optionally substituted $C_3$–$C_5$ alkenyl,
  (4) optionally substituted $C_3$–$C_5$ alkynyl,
  (5) optionally substituted $C_1$–$C_5$ alkanoyl,
  (6) optionally substituted $C_3$–$C_5$ alkenoyl,
  (7) optionally substituted $C_3$–$C_5$ alkynoyl,
  (8) optionally substituted aroyl,
  (9) optionally substituted aryl,
  (10) optionally substituted $C_5$–$C_6$ cycloalkanoyl,
  (11) optionally substituted $C_5$–$C_6$ cycloalkenoyl,
  (12) optionally substituted $C_1$–$C_5$ alkylsulfonyl
  (13) optionally substituted $C_5$–$C_6$ cycloalkyl
  (14) optionally substituted $C_5$–$C_6$ cycloalkenyl where the substitutents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 3 groups independently selected from hydroxy, $C_1$–$C_3$ alkoxy, $C_5$–$C_6$ cycloalkyl, aryl $C_1$–$C_3$ alkoxy, $NR^g R^h$, $CO_2 R^b$, $CONR^c R^d$ and halogen,
  (15) $C_1$–$C_3$ perfluoroalkyl,
  (16) arylsulfonyl optionally substituted with 1 to 3 groups independently selected from methyl, trifluoromethyl, nitro, halogen or cyano,
  (17) a 5- or 6-membered ring containing 1 to 4 heteroatoms selected from oxygen, sulfur and nitrogen optionally substituted by 1 to 4 groups independently selected from methyl, trifluoromethyl, amino, $C(O)NR^c R^d$, cyano, $CO_2 R^b$ or halogen, and which may be saturated or partly unsaturated;

$R^b$ is
  (1) H,
  (2) optionally substituted aryl,
  (3) optionally substituted $C_1$–$C_5$ alkyl,
  (4) optionally substituted $C_3$–$C_5$ alkenyl, or
  (5) optionally substituted $C_3$–$C_5$ alkynyl, where the substituents on the aryl, alkyl, alkenyl or alkynyl are from 1 to 3 groups independently selected from hydroxy, $C_1$–$C_2$ alkoxy, $C_5$–$C_6$ cycloalkyl, halogen, $C_1$–$C_3$ alkanoyloxy, $C(O)NR^c R^d$, $CO_2 R^b$, formyl, $-NR^g R^h$, optionally substituted aryl, and optionally substituted aryl $C_1$–$C_3$ alkoxy, wherein the aryl substituents are 1 to 3 groups independently selected from $R^e$;

$R^e$ is
  (1) halogen,
  (2) methyl,
  (3) trifluoromethyl,
  (4) $-S(O)_m R^i$,
  (5) cyano,
  (6) $R^j O(CH_2)_v-$,
  (7) $R^j CO_2 (CH_2)_v-$,
  (8) $R^j OCO(CH_2)_v$,
  (9) optionally substituted aryl where the substituents are from 1 to 3 of halogen, methyl, methoxy, or hydroxy;

$R^g$ and $R^h$ are independently
  (1) hydrogen,
  (2) $C_1$–$C_3$ alkyl,
  (3) aryl,
  (4) aryl $C_1$–$C_3$ alkyl,
  (5) $C_1$–$C_4$ alkoxycarbonyl,
  (6) $C_1$–$C_4$ alkylcarbonyl, or
  (7) $C_1$–$C_4$ alkanoyl $C_1$–$C_5$ alkyl; or $R^g$ and $R^h$ together with the N to which they are attached form a 5- to 6-membered ring containing 0 to 2 additional heteratoms selected from O, $S(O)_m$, and N, optionally substituted with 1 to 3 groups independently selected from $R^g$ and oxo;

$R^i$ and $R^j$ are independently
  (1) hydrogen,
  (2) trifluoromethyl,
  (3) optionally substituted $C_1$–$C_3$ alkyl, where the substituents are aryl or substituted aryl;
  (4) aryl or substituted aryl where the aryl substituents are from 1 to 3 groups independently selected from halogen, methyl, methoxy, or hydroxy; and all other groups are as defined in Claim 1.

In another aspect of the present invention there are provided compounds having the formula X

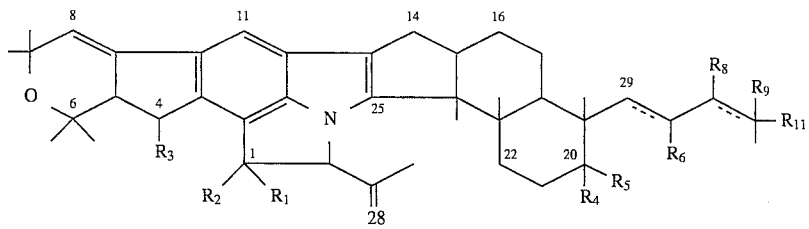

where $R_1$–$R_6$, $R_8$ and $R_9$ are as defined in Claim 1;

$R_{11}$ is
(1) COCl,
(2) $CON_3$, or
(3) NCO.

Compounds of formula X are useful as intermediates in the preparation of certain compounds of formula I form Compounds A, B and C.

Another aspect of the present invention provides a method for the treatment of helminthiasis in human and animals which comprises administering to an animal in need of such treatment an effective amount of a compound of formula I, nodulisporic acid, 29,30-dihydro-20,30-oxa-nodulisporic acid or 31-hydroxy-20,30-oxa-29,30,31,32-tetrahydro-nodulisporic acid.

"Alkyl" as well as other groups having the prefix "alk", such as alkoxy, alkanoyl, alkenyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

The term "halogen" is intended to include the halogen atoms fluorine, chlorine, bromine and iodine.

Examples of 5- or 6-membered rings containing from 1 to 4 heteroatoms independently selected from oxygen, sulfur and nitrogen include saturated heterocycles such as morpholine, thiomorpholine, piperidine, piperazine, tetrahydropyran, tetrahydrofuran, tetrahydrothiophene, oxazolidine, pyrrolidine, partly unsaturated heterocycles such as dihydropyran, dihydropyridazine, dihydrofuran, dihydrooxazole, dihydropyrazole, dihydropyridine, dihydropyridazine and the like.

The term "aryl" is intended to include phenyl, napthyl, and the like and 5- and 6-membered heteroaryls containing from 1 to 5 nitrogen, oxygen and sulfur heteroatoms, such as pyrrolyl, isoxazolidinyl, pyrazinyl, pyridinyl, oxazolyl, thiazolyl, imidazolyl, triazolyl, tetrazolyl, furanyl, triazinyl, thienyl, pyrimidinyl, pyridazinyl, pyrazinyl and the like, optionally having a benzo or pyrido ring fused thereto such as benzoxazolyl, benzothiazolyl, benzimidazolyl, benzofuranyl, benzoxazinyl, benzothiophenyl, quinolinyl, indolyl and the like.

Aroyl means arylcarbonyl in which aryl is as defined above.

Examples of $NR^cR^d$ or $NR^gR^h$ forming a 3- to 7- membered ring containing 0 to 2 additional heteroatoms selected from O, $S(O)_m$ and N are aziridine, azetidine, pyrrolidine, piperidine, thiomorpholine, morpholine, piperidine, and the like.

Certain of the above defined terms may occur more than once in the above formula and upon such occurrence each term shall be defined independently of the other; thus for example, $OR^a$ at C4 may represent OH and at C20 represent O-acyl.

Compounds described herein contain one or more asymmetric centers and may thus give rise to diastereomers and optical isomers. The present invention is intended to include all possible diastereomers as well as their racemic and resolved, enantiomerically pure forms and all possible geometric isomers. In addition, the present invention includes all pharmaceutically acceptable salts thereof.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N$^-$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, s fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Compounds of the present invention are named based on the trivial name of the parent compound, nodulisporic acid (compound A), and their position numbers are those as indicated in formula I.

Compounds of the present invention are prepared from the three nodulisporic acids (Compounds A, B and C), which in turn are obtained from the fermentation culture of Nodulisporium sp. MF-5954 (ATCC74245). The description of the producing microorganism, the fermentation process, and the isolation and purification of the three nodulisporic acids are disclosed in U.S. Pat. No. 5,399,582, issued Mar. 21, 1995, which is hereby incorporated by reference in its entirety.

The above structural formula is shown without a definitive stereochemistry at certain positions. However, during the the course of the synthetic procedures used to prepare such compounds, or using racemization or epimerization procedures known to those skilled in the art, the products of such procedures can be a mixture of stereoisomers. In particular, the stereoisomers at C1, C4, C20, C26, C31 and C32 may be oriented in either the alpha- or beta-position, representing such groups oriented below or above the plane of the molecule, respectively. In each such case, and at other positions in the molecule, both the alpha- and beta-configurations are intended to be included within the ambit of this invention.

Compounds of formula I wherein the allyl group at position 26 is in the epi configuration may be obtained by treatment of the appropriate precursor with a bases such as hydroxide, methoxide, imidazole, triethylamine, potassium hydride, lithium diisopropylamide and the like in protic or aprotic solvents (as appropriate) such as water, methanol, ethanol, methylene chloride, chloroform, tetrahydrofuran, dimethylformamide and the like. The reaction is complete at temperatures from −78° C. to the reflux temperature of the solution in from 15 minutes to 12 hours.

Compounds of formula I where $R_2$ (and $R_1$ is hydrogen), $R_3$, $R_4$ and $R_8$ independently are hydroxy may be inverted by treatment of the appropriate alcohol using protocols known to those skilled in the art. For example, the alcohol may be reacted under Mitsunobu conditions with a carboxylic acid (formic acid, propionic acid, 2-chloroacetic acid, benzoic acid, para-nitro-benzoic acid and the like), a trisubstituted phosphine (triphenylphosphine, tri-n-butylphoshine, tripropylphosphine and the like) and a dialkyl diazodicarboxylate (diethyl diazodicarboxylate, dimethyl diazodicarboxylate, diisopropyl diazodicarboxylate and the like) in an aprotic solvent such as methylene chloride, tetrahydrofuran, chloroform, benzene and the like. The Mitsunobu reactions are complete in from 1 to 24 hours at temperatures from 0° C. to the reflux temperature of the solution. The resultant esters may be hydrolized by treatment with hydroxide or ammonium hydroxide in a protic solvent such as methanol, ethanol, water, tetrahydrofuran/water or dimethylformamide/water and the like at from 0° C. to the reflux temperature of the solution. Alternatively, the resultant esters may be hydrolized by treatment with a Lewis acid, such as magnesium chloride, aluminum chloride, titanium tetra-isopropoxide and the like in a protic solvent such as methanol, ethanol, isopropanol and the like and the reactions are complete in from 1 to 24 hours at 0° C. to the reflux temperature of the solution.

During certain reactions described below, it may be necessary to protect the groups at $R_2$, $R_3$, $R_4$, $R_8$, $R_9$ and $R_{10}$. With these positions protected, the reactions may be carried out at other positions without affecting the remainder of the molecule. Subsequent to any of the described reactions (vida infra), the protecting group(s) may be removed and the unprotected product isolated. The protecting groups employed at $R_2$, $R_3$, $R_4$, $R_8$, $R_9$ and $R_{10}$ are those which may be readily synthesized, not significantly affected by the reactions at the other positions, and may be removed without significantly affecting any other functionality of the molecule. One preferred type of protecting group is the trisubstituted silyl group, preferably the tri-loweralkyl silyl group or di-loweralkyl-aryl silyl group. Especially preferred examples are the trimethylsilyl, triethylsilyl, triisopropylsilyl, tert-butyldimethylsilyl and dimethylphenylsilyl groups.

The protected compound may be prepared with the appropriately substituted silyl trifluoromethanesulfonate or silyl halide, preferably the silyl chloride. The reaction is carried out in an aprotic solvent such as methylene chloride, benzene, toluene, ethyl acetate, isopropyl acetate, tetrahydrofuran, dimethylformamide and the like. In order to minimize side reactions, there is included in the reaction mixture a base to react with the acid released during the course of the reaction. Preferred bases are amines such as imidazole, pyridine, triethylamine or diisopropylethylamine and the like. The base is required in amounts equimolar to the amount of hydrogen halide liberated, however, generally several equivalents of the amine are employed. The reaction is stirred at from 0° C. to the reflux temperature of the reaction mixture and is complete from 1 to 24 hours.

The silyl group is removed by treatment of the silyl compound with anhydrous pyridine-hydrogen fluoride in tetrahydrofuran or dimethylsulfoxide or with tetraalkylammonium fluoride in tetrahydrofuran. The reaction is complete in from 1 to 24 hours at from 0° C. to 50° C. Alternatively, the silyl group may be removed by stirring the silylated compound in lower protic solvents such as methanol, ethanol, isopropanol and the like catalyzed by an acid, preferably a sulfonic acid monhydrate such as para-toluenesulfonic acid, benzenesulfonic acid or carboxylic acids such as acetic acid, propionic acid, monochloroacetic acid, dichloroacetic acid, trichloroacetic acid and the like. The reaction is complete in 1 to 24 hours at from 0° C. to 50° C.

Protecting groups that may also be suitably used in the preparation of compounds of the present invention may be found in standard textbooks such as Greene and Wutz, *Protective Groups in Organic Synthesis*, 1991, John Wiley & Sons, Inc.

Compounds of formula I where $R_1$ and $R_2$ together represent an oxime, $=NOR^a$, may be prepared by treating the appropriate oxo analog with $H_2NOR^a$ to produce the corresponding oxime. Oxime formation may be accomplished using techniques known to those skilled in the art, including, but not restricted to, the use of $H_2NOR^a$ either as the free base or as an acid addition salt such as the HCl salt, or an O-protected hydroxylamine such as O-trialkylsilylhydroxylamine, in a protic solvent such as methanol, ethanol, isopropanol and the like or aprotic solvents such as methylene chloride, chloroform, ethyl acetate, isopropyl acetate, tetrahydrofuran, dimethylformamide, benzene, toluene and the like, as appropriate. The reactions may by catalyzed by the addition of sulfonic acids, carboxylic acids or Lewis acids, including, but not limited to, benzenesulfonic acid monhydrate, para-toluenesulfonic acid monohydrate, acetic acid, zinc chloride and the like.

Similarly, compounds of formula I wherein $R_1$ and $R_2$ together represent $=NNR^cR^d$ may be prepared by treating the appropriate oxo analog with $H_2NNR^cR^d$ to give the corresponding hydrazones using conditions directly analogous to those described for oxime formation.

Compounds of formula I wherein one or both of the ---- bonds represent a single bond may be prepared from the corresponding compound wherein ---- is a double bond by conventional hydrogenation procedures. The double bonds may be hydrogenated with any of a variety of standard precious metal hydrogenation catalysts such as Wilkinson's catalyst, Pearlman's catalyst, 1–25% palladium on carbon, 1–25% platinum on carbon and the like. The reaction is generally carried out in a non-reducible solvents (either protic or aprotic) such as methanol, ethanol, isopropanol, tetrahydrofuran, ethyl acetate, isopropyl acetate, benzene, toluene, dimethylformamide and the like. The hydrogen source may be hydrogen gas from 1 to 50 atmospheres pressure or other hydrogen sources such as ammonium formate, cyclohexene, cyclohexadiene and the like. The reduction also may be carded out using sodium dithionite and sodium bicarbonate in the presence of a phase transfer catalyst, in particular a tetraalkylammonium phase transfer catalyst, and the like. The reactions may be run from 0° C. to 100° C. and are complete in from 5 min to 24 hours.

Compounds of formula I wherein $R_8$ and $R_9$ are both hydroxyl groups may be prepared according to the procedure shown in Scheme I.

SCHEME I

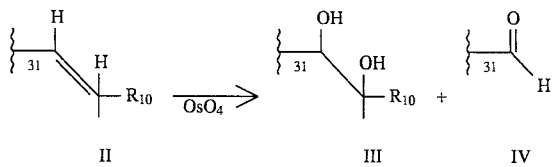

Thus, Compound II is treated with osmium tetroxide under conditions known to those skilled in the art to yield the diol product III. Also produced during this reaction is the aldehyde IV. Osmium tetroxide may be used either stoichiometrically or catalytically in the presence of an oxidant, including, but not restricted to, morpholine N-oxide, trimethylamine N-oxide, hydrogen peroxide, tert-butyl hydroperoxide and the like. The dihydroxylation reactions may be performed in a variety of solvents or mixtures of solvents. These include both protic and aprotic solvents such as water, methanol, ethanol, tert-butanol, ether, tetrahydrofuran, benzene, pyridine, acetone and the like. The reactions may be performed at from −78° C. to 80° C. and are complete in from 5 minutes to 24 hours.

Compounds of formula I wherein $R_8$ is $NR^cR^d$ and $R_9$ is hydrogen may be prepared by treatment of the appropriate precursor containing the C31–C32 unsaturation with $HNR^cR^d$ or $HCl \cdot HNR^cR^d$ in an appropriate protic or aprotic solvents such as methanol, ethanol, benzene, toluene, dimethylformamide, dioxane, water and the like. The reaction may be facilitated by the addition of bases such as pyridine, triethylamine, sodium carbonate and the like or Lewis acids such as zinc chloride, magnesium chloride and the like. The reactions are complete in from 1 to 24 hours at temperatures from 0° C. to the reflux temperature of the solution.

Compounds of formula I wherein $R_2$ is OH and $R_1$ is H may be prepared from the corresponding ketone by treating the appropriate oxo analog with standard reducing agents including, but not restricted to, sodium borohydride, lithium borohydride, lithium aluminum hydride, potassium tri-sec-butyl borohydride, diisobutylaluminum hydride, diborane oxazaborolidines and is alkylboranes (both achiral and chiral). These reactions are performed in a manner known to those skilled in the art and are carried out in non-reducible solvents such as methanol, ethanol, diethyl ether, tetrahydrofuran, hexanes, pentane, methylene chloride and the like. The reactions are complete in from 5 minutes to 24 hours at temperatures ranging from −78° C. to 60° C. Compounds of formula I wherein $R_2$ is OH, $R_1$ is H and $R_{10}$ is $CH_2OH$ may be obtained by reacting reacting the appropriate carboxylic acid or ester analog (eg. where $R_{10}$ is $CO_2H$ or $CO_2Ra$) with the more reactive reducing agents as described above, including lithium aluminum hydride, lithium borohydride and the like. Compounds of formula I wherein $R_2$ and $R_1$ together are oxo and $R_{10}$ is $CH_2OH$ may be obtained by reacting reacting the appropriate carboxylic acid (eg. where R10 is $CO_2H$) with less reactive reducing agents such as diborane and the like.

Compounds of formula I wherein $R_2$ is OH and $R_1$ is other than H, may be prepared from the corresponding ketone by treating the appropriate oxo analog with a Grignard reagent $R_1M_gBr$, or with a lithium reagent $R_1Li$. These reactions are performed in a manner known to those skilled in the art and preferably are performed in aprotic solvents such as diethyl ether, tetrahydrofuran, hexanes or pentanes. The reactions are complete in from 5 minutes to 24 hours at temperatures ranging from −78° C. to 60° C.

Compounds of formula I where $R_{10}$ is $C(O)N(OR^b)R^c$ or $C(O)NR^cR^d$ are prepared from the corresponding carboxylic acid using standard amide-forming reagents known to those skilled in the art. The reaction is carried out using at least one equivalent of an amine nucleophile, $HN(OR^b)R^c$ or $HNR^cR^d$, although preferably ten to one hundred equivalents of amine nucleophiles are employed. Amide-forming reagents include, but are not restricted to, dicyclohexylcarbodiimide, 1-(3-dimethylaminopropyl)-3-ethylcarbodiimide hydrochloride (EDC•HCl), diisopropylcarbodiimide, benzotriazol-1-yloxy-tris(dimethylamino)phosphonium hexafluorphosphate (BOP), bis(2-oxo-3-oxazolidinyl)phosphinic chloride (BOP–Cl), benzotriazole-1-yl-oxy-tris-pyrrolidinox phosphonium hexafluorophosphate (PyBOP), chloro-tris-pyrrolidinophosphonium hexafluorophosphate (PyCloP), bromo-tris-pyrrolidinophosphonium hexafluorophosphate (PyBroP), diphenylphosphoryl azide (DPPA), 2-(1H-benzotriazole-1-yl)-1,1,3,3-tetramethyluronium hexafluorophosphate (HBTU), O-benzotriazol-1-yl-N,N,N',N'-bis(pentamethylene)uronium hexafluorophosphate and 2-chloro-1-methylpyridinium iodide. The amide-forming reactions may be facilitated by the optional addition of N-hydroxybenzotriazole or N-hydroxy-7-aza-benzotriazole. The amidation reaction is generally performed using at least one equivalent (although several equivalents may be employed) of amine bases such as triethylamine, diisopropylethylamine, pyridine, N,N-dimethylaminopyridine and the like. The carboxyl group may be activated for amide bond formation via its corresponding acid chloride or mixed anhydride, using conditions known to those skilled in the art. These amide-forming reactions are carried out in aprotic solvents such as methylene chloride, tetrahydrofuran, diethyl ether, dimethylformamide, N-methylpyrrolidine and the like at −20° C. to 60° C. and are complete in 15 minutes to 24 hours.

Compounds of formula I where $R_{10}$ is cyano may be prepared by treatment of the appropriate carboxamide with dehydrating reagents known to those skilled in the art such para-toluenesulfonyl chloride, methanesulfonyl chloride, acetyl chloride, thionyl chloride, phosphorus oxychloride or catecholboron chloride in an aprotic solvent such as methylene chloride, chloroform, tetrahydrofuran, benzene, toluene and the like. The reactions are complete in from 15 minutes to 24 hours at temperatures from −78° C. to the reflux temperature of the solution.

Compounds of formula I where $R_{10}$ is $C(O)OR^b$ are prepared from the corresponding carboxylic acid using standard ester-forming reagents known to those skilled in the art. The esterification reaction is carded out using at least one equivalent of an alcohol, $HOR^b$, although preferably ten to one hundred equivalents of alcohol are used; the esterification also may be carded out using the alcohol as solvent. Esterification reagents include, but are not restricted to, dicyclohexylcarbodiimide, 1-(3-dimethylaminopropyl)-3-ethylcarbodiimide hydrochloride (EDC•HCl), diisopropylcarbodiimide, benzotriazol-1-yloxy-tris(dimethylamino)phosphonium hexafluorphosphate (BOP), bis(2-oxo-3-oxazolidinyl)phosphinic chloride (BOP-Cl), benzotriazole-1-yl-oxy-tris-pyrrolidinophosphonium hexafluorophosphate (PyBOP), chloro-tris-pyrrolidinophosphonium hexafluorophosphate (PyCloP), bromo-tris-pyrrolidinophosphonium hexafluorophosphate (PyBroP), diphenylphosphoryl azide (DPPA), 2-(1H-benzotriazole-loyl)-1,1,3,3-tetramethyluronium hexafluorophosphate (HBTU), O-benzotriazol-1-yl-N,N,N',N'-bis(pentamethylene)uronium hexafluorophosphate and 2-chloro-1-methylpyridinium iodide. The ester-forming reactions may be facilitated by the optional addition of N-hydroxybenzotriazole, N-hydroxy-7-aza-benzotriazole, 4-(N,N-dimethylamino)pyridine or 4-pyrrolidinopyridine.

The reaction is generally performed using at least one equivalent (although several equivalents may be employed) of amine bases such as triethylamine, diisopropylethylamine, pyridine and the like. The carboxyl group may be activated for ester bond formation via its corresponding acid chloride or mixed anhydride, using conditions known to those skilled in the art. These ester-forming reactions are carded out in aprotic solvents such as methylene chloride, tetrahydrofuran, diethyl ether, dimethylformamide, N-methylpyrrolidine and the like at temperatures ranging from $-20°$ C. to $60°$ C. and are complete in 15 minutes to 24 hours.

Compounds of formula I wherein one or more of $R_2$, $R_3$, $R_4$, $R_8$ and $R_9$ is $OR^a$, $OCO_2R^b$ or $OC(O)NR^cR^d$, and/or where $R_{10}$ is $CH_2OR^a$, $CH_2OCO_2R^b$ or $CH_2OC(O)NR^cR^d$ may be prepared using known methods for acylation, sulfonylation and alkylation of alcohols. Thus, acylation may be accomplished using reagents such as acid anhydrides, acid chlorides, chloroformates, carbamoyl chlorides and amine bases according to general procedures known to those skilled in the art. Sulfonylations may be carried out using sulfonylchlorides or sulfonic anhydrides. The acylation and sulfonylation reactions may be carried out in aprotic solvents such as methylene chloride, chloroform, pyridine, benzene, toluene and the like. The acylation and sulfonylation reactions are complete in from 15 minutes to 24 hours at temperatures ranging from $-20°$ C. to $80°$ C.

Compounds of formula I wherein one or more of $R_2$, $R_3$, $R_4$, $R_8$ and $R_9$ is $OR^a$ and/or where $R_{10}$ is $CH_2OR^a$, may be prepared using methods known to those skilled in the art for the alkylation of alcohols. Thus, alkylation may be accomplished using reagents including, but not restricted to, halides $IR^a$, $BrR^a$, $ClR^a$, diazo reagents $N_2R^a$, trichloroacetimidates $R^aOC(NH)CCl_3$, sulfates $R^aOSO_2M^e$, $R^aOSO_2CF_3$, and the like. The alkylation reactions may be facilitated by the addition of acid, base or Lewis acids, as appropriate. The reactions are performed in aprotic solvents such as methylene chloride, chloroform, tetrahydrofuran, benzene, toluene, dimethylformamide, N-methyl-pyrrolidine, dimethyl sulfoxide, hexamethylphosphoramide and are complete at from $0°$ C. to the reflux temperature of the solution and are complete in from 15 minutes to 48 hours.

Compounds of formula I where $R_{10}$ is $NHC(O)OR^b$ or $C(O)NR^bR^c$ are prepared from the corresponding carboxylic acid via the corresponding acyl azide (VI) and isocyanate (VII) as shown in Scheme II.

SCHEME II

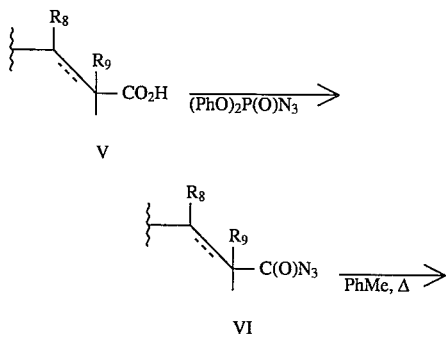

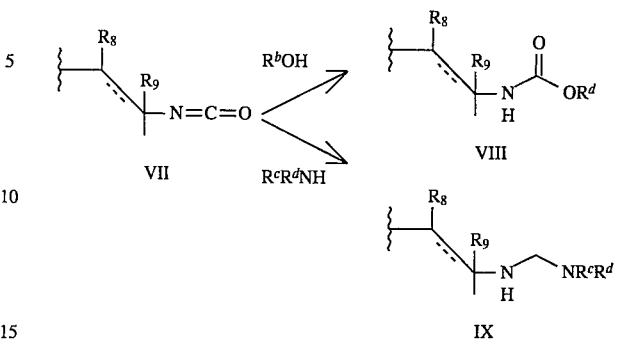

In Scheme II, $R_8$, $R_9$, $R^a$, $R^c$ and ---- have the same meaning as defined under formula I. Thus, the carboxylic acid (compound V) is treated with diphenylphosphoryl azide to provide the acyl azide (compound VI). Heating of compound VI in an aprotic solvent such as benzene, toluene, dimethylformamide and the like results in a rearrangement yielding compound VII, an isocyanate. Compound VII may be reacted in an aprotic solvent such as benzene, toluene, methylene chloride, 1,2-dichloroethylene, dimethylformamide and the like, with an alcohol $R^bOH$, such as methanol, ethanol, benzyl alcohol, 2-trimethylsilylethanol, 2,2,2-trichloroethanol, methyl glyocolate, phenol and the like to yield compound VIII, a carbamate. The addition of one or more equivalents of an amine base such as triethylamine, diisopropylethylamine, pyridine and the like may be employed to accelerate carbamate formation. The carbamate-forming reactions may be performed from $0°$ C. to $100°$ C. and are complete in 15 minutes to 24 hours.

Compounds of formula IX may be prepared when compounds of formula VII are reacted with an appropriate amine $HNR^cR^d$ in an aprotic solvent such as methylene chloride, tetrahydrofuran, dimethylformamide, dimethylsulfoxide, benzene, toluene and the like. The urea-forming reactions may be performed from $0°$ C. to $100°$ C. and are complete in 15 minutes to 24 hours.

The instant compounds are potent endo- and ectoantiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry.

Among the helminths, the group of worms described as nematodes causes widespread and often times serious infection in various species of animals. The most common genera of nematodes infecting the animals referred to above are Haemonchus, Trichostrongylus, Ostertagia, Nematodirus, Coopefta, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Coopefta, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites such as scabies lice, fleas, blowflies, and other biting insects in domesticated animals and poultry, such as Tenophalides, Ixodes, Psoroptes, and Hemotobia, in sheep Lucilia sp., biting insects and such migrating dipterous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carder vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 200 mg per kg of animal body weight, such total dose being given at one time or in divided doses over a relatively short period of time such as 1–5 days. With the preferred compounds of the invention, excellent control of such parasites is obtained in animals by administering from about 0.025. to 50 mg per kg of body weight in a single dose. Repeat treatments are given as required to combat reinfections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carder or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compotinds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided to more fully illustrate the present invention, and shall not be construed as limiting the scope in any manner.

EXAMPLE 1

Methyl nodulisporate

To 5.4 mg nodulisporic acid in 5 mL methanol at room temperature was added 0.5 mL 10% trimethylsilyldiazomethane in hexanes. After 15 minutes, three drops of glacial acetic acid was added and the solution diluted with benzene, frozen and liophilized. Pure methyl ester was obtained following reversed-phase HPLC purification using 85:15 methanol:water as eluant and the product was characterized by $^1$H NMR and MS.

EXAMPLE 2

N-Methyl nodulisporamide and 26-epi-N-methyl nodulisporamide

To 1 mg nodulisporic acid in 1 mL dimethylformamide at room temperature was added 2 mg HCl•H$_2$NMe, 2 mg N-hydroxybenzotriazole and 10 µL diisopropylethylamine to which was added 2 mg EDC•HCl. After 30 minutes, the reaction was quenched by addition of methanol and 1 drop glacial acetic acid. The solution was diluted with brine, extracted with ethyl acetate, dried with Na$_2$SO$_4$, filtered and concentrated under reduced pressure. The reaction was partially purified by preparative TLC (1×0.5 mm silica gel plate) using 6:3:1 EtOAc/acetone/methanol. N-Methyl nodulisporamide and 26-epi-N-methyl nodulisporamide were purified to homogeniety by reversed-phase HPLC using a 60 minute linear gradient from 25:75 to 100:0 acetonitrile/water. The purified products were characterized by $^1$H NMR and MS.

EXAMPLE 3

Nodulisporyl azide

To 1 mg of nodulisporic acid in 0.2 mL chloroform was added 50 µL triethylamine and 20 µL of diphenylphosphoryl azide. The reaction mixture was stirred at room temperature for 3h before purification on silica gel (preparative TLC, 1×0.5 mm silica gel) using 1:1 EtOAc/hexanes to yield 0.8 mg of pure product which was characterized by $^1$H NMR and MS.

EXAMPLE 4

N-(n-Propyl) nodulisporamide

To 0.5 mg nodulisporic acid in 1 mL methylene chloride at room temperature was added 2 drops diisopropylethylamine, 5 mg H$_2$NCH$_2$CH$_2$CH$_3$, 3 mg N-hydroxylbenzotriazole and 3 mg PyBOP. After 30 minutes at room temperature, the reaction was quenched with 2 mL saturated NaHCO$_3$, extracted with ethyl acetate, dried (Na$_2$SO$_4$), filtered and concentrated in vacuo. The crude was partially purified by silica gel flash chromatography using 0.5:5:95 NH$_4$OH/MeOH/CHCl$_3$ as eluant followed by reversed-phase HPLC purification using 20:80 water/methanol as eluant. The product was characterized by $^1$H NMR.

EXAMPLE 5

(4-morpholinyl)-nodulisporamide

To 1.5 mg nodulisporic acid in 1 mL methylene chloride at room temperature was added 1 drop diisopropylethylamine, 1 drop morpholine and 2 mg N-hydroxybenzotriazole. 2 mg pyBOP was then added. After 1 hour at RT, the solution was filtered through 2 inches silica gel in a pipet without workup using ethyl acetate as eluant. The resultant solution was concentrated under reduced pressure and pure product was obtained following reversed-phase HPLC using 20:80 water/MeOH as eluant. The product was characterized by $^1$H NMR.

EXAMPLE 6

N-(2-hydroxyethyl)-nodulisporamide

To 0.5 mg nodulisporic acid in 1 mL methylene chloride at room temperature was added 2 drops diisopropylethylamine, 5 mg $H_2NCH_2CH_2OH$, 3 mg N-hydroxybenzotriazole and 3 mg PyBOP. After 30 minutes, the reaction was quenched with 2 mL saturated $NaHCO_3$, extracted with ethyl acetate, dried ($Na_2SO_4$), filtered and concentrated in vacuo. The crude was purified by reversed-phase HPLC using 20:80 water/methanol as eluant and the product was characterized by $^1H$ NMR.

EXAMPLE 7

N-(2-methoxycarbonyl-3-methoxypropyl)-nodulisporamide

To 1.5 mg nodulisporic acid in 1 mL methylene chloride at room temperature was added 2 drops diisopropylethylamine, 5 mg $HCl \cdot H_2NCH(CH_2OH)CO_2Me$, 3 mg N-hydroxybenzotriazole and 3 mg PyBOP. After 30 minutes, the reaction was quenched with 2 mL saturated $NaHCO_3$, extracted with ethyl acetate, dried ($Na_2SO_4$), filtered and concentrated in vacuo. Pure product was obtained following reversed-phase HPLC using 20:80 water/methanol as eluant and the product was characterized by $^1H$ NMR.

EXAMPLE 8

Nodulisporamide and 31-amino-31,32-dihydro-nodulisporamide

To 1.5 mg nodulisporic acid in 1 mL methylene chloride at room temperature was added 1 drop diisopropylethylamine, 1 drop $NH_4OH$ and 2 mg N-hydroxybenzotriazole. To this was added 3 mg PyBOP and the solution was stirred for 15 min. The reaction was quenched with 2 mL saturated $NaHCO_3$, extracted with ethyl acetate, s dried with $Na_2SO_4$, filtered and concentrated in vacuo. Pure nodulisporamide was obtained following preparative TLC (1×0.5 mm silica gel) using 1:9 methanol/chloroform as eluant. Nodulisporamide was characterized by $^1H$ NMR. Also obtained from this reaction was 31-amino-31,32-dihydro-nodulisporamide.

EXAMPLE 9

N-(methoxy carbonylmethyl)-nodulisporamide

To 1.5 mg nodulisporic acid in 1 mL methylene chloride at room temperature was added 1 drop diisopropylethylamine, 2 mg N-hydroxybenzotriazole and 2 mg $HCl \cdot H_2NCH_2CO_2Me$. To this solution was added 2 mg PyBOP. After 30 min, the reaction was quenched with 2 mL saturated $NaHCO_3$, extracted with ethyl acetate, dried using $Na_2SO_4$, filtered and concentrated under reduced pressure. Pure product was obtained following reversed-phase HPLC purification using 17.5:82.5 water/methanol as eluant. The product was characterized by $^1H$ NMR and MS.

EXAMPLE 10

N,N-tetramethylene-nodulisporamide

To 125 mg nodulisporic acid in 10 mL methylene chloride at 0° C. was added 0.18 mL diisopropylethylamine, $HCl \cdot H_2NCH_2CO_2Me$ followed by 108 mg PyBOP. After 5 minutes, the solution was warmed to room temperature. After 1.5 hours, the solution was poured in 25 mL saturated $NaHCO_3$, extracted with methylene chloride, dried with $Na_2SO_4$, filtered and concentrated under reduced pressure. Pure N-N-tetramethylene-nodulisporamide was obtained following reversed-phase HPLC purification using 50:50 acetonitrile/water as eluant (isocratic for ten min), followed by a linear 30 minute gradient to 75:25 acetonitrile/water. Pure product (26 mg) was characterized by $^1H$ NMR and MS.

EXAMPLE 11

Methyl 29,30-dihydro-20,30-oxa-nodulisporic acid

To 0.8 mg Compound B in 1 mL methanol at room temperature was added 0.2 mL 1M trimethylsilyldiazomethane in hexanes. After 5 minutes, 0.1 mL glacial acetic acid was added, the solution stirred for three minutes and the 2 mL saturated $NaHCO_3$ was added (foaming occurred). The solution was extracted with ethyl acetate, dried with $Na_2SO_4$, filtered and concentrated in vacuo. The crude was purifed by reversed-phase HPLC using 15:85 water/methanol as eluant and the purified product was characterized by $^1H$ NMR.

EXAMPLE 12

N-Ethyl 29,30-dihydro-20,30-oxa-nodulisporamide

To 1 mg Compound B in 1 mL methylene chloride at room temperature was added 1 drop diisopropylethylamine, 1 drop $CH_3CH_2NH_2$, 3 mg N-hydroxybenzotriazole and 3 mg PyBOP. After 15 minutes, the reaction was quenched with 2 mL saturated $NaHCO_3$, extracted with ethyl acetate, dried with $Na_2SO_4$, filtered and concentrated in vacuo. The crude was purified by reversed-phase HPLC using 15:85 water/methanol as eluant and the purified product was characterized by $^1H$ NMR.

EXAMPLE 13

N-(2-hydroxyethyl)-29,30-dihydro-20,30-oxa-nodulisporamide

To 0.7 mg Compound B in 1 mL methylene chloride at room temperature was added 1 drop diisopropylethylamine, 1 drop $HOCH_2CH_2NH_2$, 3 mg N-hydroxybenzotriazole and 3 mg PyBOP. After 15 minutes, the reaction was quenched with 2 mL saturated $NaHCO_3$, extracted with ethyl acetate, dried with $Na_2SO_4$, filtered and concentrated in vacuo. The crude was purified by reversed-phase HPLC using first 20:80 water/methanol then 15:85 water/methanol as eluant and the purified product was characterized by $^1H$ NMR.

EXAMPLE 14

Methyl 31-hydroxy-20,30-oxa-29,30,31,32-tetrahydronodulisporate

To 1 mg Compound C in 1 mL methanol at room temperature was added 0.2 mL 1M trimethylsilyldiazomethane in hexanes. After 5 minutes, 0.1 mL glacial acetic acid was added, the solution stirred for three minutes and the 2 mL saturated $NaHCO_3$ was added (foaming occurred). The solution was extracted with ethyl acetate, dried with $Na_2SO_4$, filtered and concentrated in vacuo. The crude was purifed by reversed-phase HPLC using 17.5:82.5 water/methanol as eluant and the purified product was characterized by $^1H$ NMR.

EXAMPLE 15

N-(2-Hydroxyethyl)-31-hydroxy-20,30-oxa-29,30,31,32-tetrahydronodulisporamide To 1 mg Compound C in 1 mL methylene chloride at room temperature was added 1 drop diisopropylethylamine, 1 drop HOCH$_2$CH$_2$NH$_2$, 3 mg N-hydroxybenzotriazole and 3 mg PyBOP. After 15 minutes, the reaction was quenched with 2 mL saturated NaHCO$_3$, extracted with ethyl acetate, dried with Na$_2$SO$_4$, filtered and concentrated in vacuo. The crude was purified by reversed-phase HPLC using first 20:80 water/methanol as eluant and the purified product was characterized by $^1$H NMR.

EXAMPLE 17

Methyl 29,30,31,32-tetrahydronodulisporate

To 1.3 mg methyl nodulisporate in 2 mL 1:1 benzene/water at room temperature was added 1 drop Adogen 464, 10 mg NaHCO$_3$ and 10 mg Na$_2$S$_2$O$_4$. The solution was heated to 80° C. for 10 minutes. The reaction was cooled to room temperature, extracted with ethyl acetate, dried with Na$_2$SO$_4$, filtered and concentrated under reduced pressure. Purified product was obtained following preparative TLC (1×0.5 mm silica gel) using 6:4 EtOAc/hexanes as eluant. The purified product was characterized by $^1$H NMR.

EXAMPLE 18

1-Hydroxy-Nodulisporic acid, methyl ester

To 0.5 mg methyl nodulisporate in 1 mL methanol at 0° C. was added 1 mg NaBH$_4$. After 10 min at 0° C., the solution was purified by reversed-phase HPLC without workup using 30:70 to 15:85 (25 minute linear gradient) water/methanol to yield pure product. The product was characterized by $^1$H NMR.

EXAMPLE 19

1-Hydroxy-32-descarboxy-32-hydroxymethyl-nodulisporic acid

To 1.2 mg methyl nodulisporate in 1.2 mL tetrahydrofuran at −78° C. was added 20 µL 1M lithium aluminum hydride in tetrahydrofuran. The yellow color rapidly disappeared. After 10 minutes, the reaction was quenched at −78° C. by dropwise addition of saturated Na$_2$SO$_4$. The solution was extracted with ethyl acetate, dried with Na$_2$SO$_4$, filtered and concentrated under reduced pressure. Pure product was obtained following preparative TLC (1×0.25 mm silica gel plate) using 85:15 EtOAc/hexanes as eluant. The purified product was characterized by $^1$H NMR.

EXAMPLE 20

32-Descarboxy-32-isocyanato-nodulisporic acid

A solution of 54 mg of nodulisporyl azide in toluene was heated at 90° C. for 2 h. The solvent was then evaporated and the isocyanate product was obtained in quantitative yield characterized by its $^1$H NMR and MS.

EXAMPLE 21

32-Descarboxy-32-(1-carbomethoxyamino)-nodulisporic acid

To 1.3 mg of isocyanate of Example 20 in 1 mL of methanol was added 20 microliters of triethylamine. The reaction mixture was heated for 45 min at 75° C. and the carbamate product 0.7 mg was isolated by preparative TLC on silica gel (1×0.5 mm) and characterized by its $^1$H NMR and MS.

EXAMPLE 22

32-Descarboxy-32-(1-(3-benzyl)urea)-nodulisporic acid

To 1 mg of isocyanate of Example 20 in 0.2 mL of toluene was added 40 microliters of benzylamine. The mixture was stirred at 20° C. for 20 min and the urea product (0.2 mg) was isolated by preparative TLC (1×0.5 mm silica gel, 1:3 hexane:EtOAc) and characterized by its $^1$H NMR and MS.

The general procedure of Example 22 was repeated using the appropriate amine to provide urea compounds of Table I.

TABLE I

32-Descarboxy-32-[UREA]-nodulisporic acid

| Example | Urea |
| --- | --- |
| 23 | NHC(O)-morpholino |
| 24 | NHC(O)NHCH$_2$Ph(4-OMe) |
| 25 | NHC(O)NHCH(Me)$_2$ |
| 26 | NHC(O)NH(CH$_2$)$_5$NH$_2$ |
| 27 | NHC(O)NHCH$_2$CH$_2$OH |
| 28 | NHC(O)NHCH$_2$CH$_2$NMe$_2$ |
| 29 | NHC(O)NHCH$_2$CH$_2$CH$_2$-morpholino |
| 30 | NHC(O)NHCH$_2$-(2-pyridyl) |
| 31 | NHC(O)NHCH$_2$CH$_2$-piperazino |

EXAMPLE 32

31,32-Dihydro-31,32-dihydroxyonodulisporic acid

To 3 mg of nodulisporic acid was added 1 mL of methanol and 100 microliters of 0.04M OsO$_4$ in t-butanol stabilized with 1% t-butyl hydroperoxide. After 50 min at room temperature, 400 mg of sodium sulfite in 2 mL of water was then added to the reaction mixture and stirring was continued for another 20 minutes. The mixture was then extracted with EtOAc and the crude products were purified by preparative TLC (1×0.5 mm silica gel plate) eluted in 95:5:0.5 dichloromethane:methanol:acetic acid to yield the title compound (1 mg isomer A and 0.6 mg isomer B) and 0.5 mg of aldehyde derived from nodulisporic acid (compound IV), each characterized by $^1$H NMR.

EXAMPLE 33

4,20-bis-O-acetyl-nodulisporic acid

To 1.2 mg of nodulisporic acid was added 300 microliters of acetic anhydride and 100 microliters of pyridine. The reaction mixture was heated at 65° C. for 1 h and excess solvent was removed in vacuo. The residual solid was purified by preparative TLC on silica gel eluted with 95:5 dichloromethane:methanol to yield 1.2 mg of the bis acetate characterized by its $^1$H NMR.

EXAMPLE 34

1-Hydroxy-nodulisporic acid

To 2.8 mg of nodulisporic acid in 0.8 mL of THF at 0° C. under argon was added 100 microliters of 2.0M lithium borohydride in THF. The reaction was quenched with 400 microliters of 2N HCl after 5 rain at 0° C. and the products were extracted with EtOAc. The extracts were dried over sodium sulfate aand concentrated in vacuo. The residual solid was purified by preparative TLC (1×0.5 mm silica gel plate, 95:5:0.5 dichloromethane:methanol:acetic acid) to yield 0.8 mg of isomer A and 0.6 mg of isomer B characterized by their $^1$H NMR and MS.

EXAMPLE 35

29,30-Dihydro-nodulisporic acid

To 1 mg of nodulisporic acid in 1 mL of dichloromethane was added 1.6 mg of Wilkinson's catalyst. The mixture was stirred under a balloon atmosphere of hydrogen overnight (18 h). HPLC separation was obtained with a Magnum 9-ODS reverse phase column and 85:15 methanol:water to 100% methanol gradient. The purified product was isolated upon evaporation of the solvent and characterized by its $^1$H NMR.

EXAMPLE 36

1-Hydroxy-1-methyl-nodulisporic acid

To 0.5 mL of 1.4M methylmagnesium bromide in THF/toluene at 0° C. was added 1 mg of nodulisporic acid dissolved in 0.6 mL of THF. After 10 min, the reaction was quenched with 2N HCl and extracted with EtOAc. Preparative TLC (1×0.5 turn silica gel plate, 95:5:0.5 dichloromethane:methanol:acetic acid) gave 0.8 mg of product characterized by its $^1$H NMR.

EXAMPLE 37

1-Hydroxy-1-methyl-nodulisporic acid, methyl ester

To 1.2 mg of methyl nodulisporate in 1 mL of THF under argon at −78° C. was added 0.5 mL of 1.4M methylmagnesium bromide in THF/toluene. The mixture was stirred for 15 min before an aqueous solution of ammonium chloride was added. The mixture was extracted with EtOAc. Preparative TLC (1×0.5 mm silica gel plate, 2:3 hexane:EtOAc) gave 1 mg of the titled product characterized by its $^1$H NMR.

What is claimed is:

1. A method for the treatment of helminthiasis in animals which comprises administering to an animal in need of such treatment an effective amount of a compound of formula I:

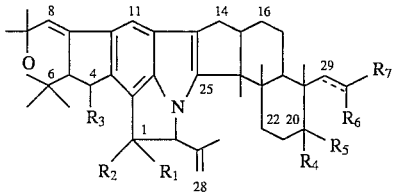

wherein $R_1$ is
  (1) hydrogen,
  (2) optionally substituted $C_1$–$C_{10}$ alkyl,
  (3) optionally substituted $C_2$–$C_{10}$ alkenyl,
  (4) optionally substituted $C_2$–$C_{10}$ alkynyl,
  (5) optionally substituted $C_3$–$C_8$ cycloalkyl,
  (6) optionally substituted $C_5$–$C_8$ cycloalkenyl
where the substitutents on the alkyl, alkenyl, alkynyl, cycloalkyl and cycloalkenyl are 1 to 3 groups independently selected from $C_1$–$C_5$ alkyl, $C_1$–$C_{10}$ alkoxy, $C_1$–$C_{10}$ alkylthio, $C_1$–$C_{10}$ alkylsulfonyl, $C_3$–$C_8$ cycloalkyl, hydroxy, halogen, cyano, carboxy, amino, $C_1$–$C_{10}$ monoalkylamino, $C_1$–$C_{10}$ dialkylamino, $C_1$–$C_{10}$ alkanoyl amino and benzoyl amino wherein said benzoyl is optionally substituted with 1 to 3 groups independently selected from $C_1$–$C_4$ alkyl, $C_1$–$C_4$ alkoxy, $C_1$–$C_4$ alkylthio, $C_2$–$C_4$ alkenyl, $C_2$–$C_4$ alkynyl, $C_1$–$C_3$-perfluoroalkyl, amino, hydroxy, halogen, $C_1$–$C_5$ monoalkylamino, $C_1$–$C_5$ dialkylamino and $C_1$–$C_5$ alkanoyl amino,
  (7) phenyl $C_0$–$C_5$ alkyl wherein said phenyl is optionally substituted with 1 to 3 groups independently selected from $C_1$–$C_4$ alkyl, $C_1$–$C_4$ alkoxy, $C_1$–$C_4$ alkylthio, $C_2$–$C_4$ alkenyl, $C_2$–$C_4$ alkynyl, $C_1$–$C_3$-perfluoroalkyl, amino, hydroxy, carboxy, halogen, $C_1$–$C_5$ monoalkylamino, $C_1$–$C_5$ dialkylamino and $C_1$–$C_5$ alkanoyl amino,
  (8) $C_1$–$C_5$ perfluoroalkyl,
  (9) a 5- or 6-membered ring selected from morpholino, pyridyl and piperazino, optionally substituted by 1 to 3 groups independently selected from hydroxy, oxo, $C_1$–$C_{10}$ alkyl and halogen, $R_2$, $R_3$, and $R_4$ are independently $OR^a$, $OCO_2R^b$, $OC(O)NR^cR^d$; or $R_1$+$R_2$ represent =O, =NOR$^a$ or =N—NR$^c$R$^d$;

$R_5$ and $R_6$ are H; or $R_5$ and $R_6$ together represent —O—;

$R_7$ is
  (1) CHO, or
  (2) the fragment

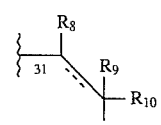

$R_8$ is independently
  (1) H, or
  (2) OR$^a$;
  (3) NR$^c$R$^d$ $R_9$ is independently
  (1) H, or
  (2) OR$^a$;

$R_{10}$ is
  (1) CN,
  (2) C(O)OR$^b$,
  (3) C(O)N(OR$^b$)R$^c$,
  (4) C(O)NR$^c$R$^d$,
  (5) NHC(O)OR$^b$,
  (6) NHC(O)NR$^c$R$^d$,
  (7) CH$_2$OR$^a$,
  (8) CH$_2$OCO$_2$R$^b$, or
  (9) CH$_2$OC(O)NR$^c$R$^d$;

---- represents a single or a double bond;

$R^a$ is
  (1) hydrogen,
  (2) optionally substituted $C_1$–$C_{10}$ alkyl,
  (3) optionally substituted $C_3$–$C_{10}$ alkenyl,
  (4) optionally substituted $C_3$–$C_{10}$ alkynyl, (5) optionally substituted $C_1$–$C_{10}$ alkanoyl,
(6) optionally substituted $C_3$–$C_{10}$ alkenoyl,
(7) optionally substituted $C_3$–$C_{10}$ alkynoyl,
(8) optionally substituted benzoyl,
(9) optionally substituted phenyl,
(10) optionally substituted $C_3$–$C_7$ cycloalkanoyl,
(11) optionally substituted $C_4$–$C_7$ cycloalkenoyl,
(12) optionally substituted $C_1$–$C_{10}$ alkylsulfonyl
(13) optionally substituted $C_3$–$C_8$ cycloalkyl
(14) optionally substituted $C_5$–$C_8$ cycloalkenyl where the substituents on the alkyl, alkenyl, alkynyl, alkanoyl, alkenoyl, alkynoyl, benzoyl, phenyl, cycloalkanoyl, cycloalkenoyl, alkylsulfonyl, cycloalkyl and cycloalkenyl are from 1 to 5 groups independently selected from hydroxy, $C_1$–$C_6$ alkoxy, $C_3$–$C_7$ cycloalkyl, aryl $C_1$–$C_3$ alkoxy, $NR^gR^h$, $CO_2R^b$, $CONR^cR^d$ and halogen,

(15) $C_1$–$C_5$ perfluoroalkyl,
(16) phenylsulfonyl optionally substituted with 1 to 3 groups independently selected from $C_1$–$C_5$ alkyl, $C_1$–$C_5$ perfluoroalkyl, nitro, halogen or cyano,
(17) a 5- or 6-membered ring selected from piperidino, morpholino, pyridyl and piperazino optionally substituted by 1 to 4 groups independently selected from $C_1$–$C_5$ alkyl, $C_1$–$C_5$ alkenyl, $C_1$–$C_5$ perfluoroalkyl, amino, $C(O)R^cR^d$, cyano, $CO_2R^b$ or halogen;

$R^b$ is
(1) H,
(2) optionally substituted phenyl,
(3) optionally substituted $C_1$–$C_{10}$ alkyl,
(4) optionally substituted $C_3$–$C_{10}$ alkenyl, or
(5) optionally substituted $C_3$–$C_{10}$ alkynyl, where the substituents on the phenyl, alkyl, alkenyl or alkynyl are from 1 to 5 groups independently selected from hydroxy, $C_1$–$C_6$ alkoxy, $C_3$–$C_7$ cycloalkyl, halogen, $C_1$–$C_5$ alkanoyloxy, $C(O)NR^cR^d$, $CO_2R^b$, formyl, —$NR^gR^h$, optionally substituted phenyl, and optionally substituted phenyl $C_1$–$C_3$ alkoxy, wherein the phenyl substituents are 1 to 3 groups independently selected from $R^e$;

$R^c$ and $R^d$ are independently $R^b$; or
$R^c$ and $R^d$ together with the N to which they are attached form a piperidino, morpholino or piperazino optionally substituted with 1 to 3 groups independently selected from $R^g$ and oxo;

$R^e$ is
(1) halogen,
(2) $C_1$–$C_7$ alkyl,
(3) $C_1$–$C_3$ perfluoroalkyl,
(4) —$S(O)_mR^i$,
(5) cyano,
(6) nitro,
(7) $R^jO(CH_2)_v$—,
(8) $R^jCO_2(CH_2)_v$—,
(9) $R^jOCO(CH_2)_v$,
(10) optionally substituted phenyl where the substituents are from 1 to 3 of halogen, $C_1$–$C_6$ alkyl, $C_1$–$C_6$ alkoxy, or hydroxy;

v is 0 to 3;

$R^g$ and $R^h$ are independently
(1) hydrogen,
(2) $C_1$–$C_6$alkyl,
(3) aryl,
(4) aryl $C_1$–$C_6$ alkyl,
(5) $C_1$–$C_5$ alkoxycarbonyl,
(6) $C_1$–$C_5$ alkylcarbonyl, or (7) $C_1$–$C_5$ alkanoyl $C_1$–$C_6$ alkyl; or $R^g$ and $R^h$ together with the N to which they are attached form a piperidino, morpholino or piperazino optionally substituted with 1 to 3 groups independently selected from $R^g$ and oxo;

$R^i$ and $R^j$ are independently
(1) hydrogen,
(2) $C_1$–$C_3$ perfluoroalkyl,
(3) optionally substituted $C_1$–$C_6$ alkyl, where the substituents are aryl or substituted phenyl;
(4) phenyl or substituted phenyl where the substituents are from 1 to 3 groups independently selected from halogen, $C_1$–$C_6$ alkyl, $C_1$–$C_6$ alkoxy, or hydroxy;

m is 0 to 2; or
a pharmaceutically acceptable salt thereof.

2. A method of claim 1 wherein the helminthiasis is due to an organism belonging to the genus Haemonchus, Bunostomum, Ancylostoma or Uncinaria.

3. A method for the treatment of helminthiasis in animals which comprise administering to an animal in need of such treatment an effective amount of a compound selected from the group consisting of Methyl nodulisporate;

N-Methyl nodulisporamide and 26-epi-N-methyl nodulisporamide;

Nodulisporyl azide;

N-(n-Propyl) nodulisporamide;

(4-morpholinyl)-nodulisporamide;

N-(2-hydroxyethyl)-nodulisporamide;

N-(2-methoxycarbonyl-3-methoxypropyl)-nodulisporamide;

Nodulisporamide and 31-amino-31,32-dihydro-nodulisporamide;

N-(methoxycarbonylmethyl)-nodulisporamide;

N,N-tetra ethylene-nodulisporamide;

Methyl 29,30-dihydro-20,30-oxa-nodulisporic acid;

N-Ethyl 29,30-dihydro-20,30-oxa-nodulisporamide;

N-(2-hydroxyethyl)-29,30-dihydro-20,30-oxa-nodulisporamide;

Methyl 31-hydroxy-20,30-oxa-29,30,31,32-tetrahydronodulisporate;

N-(2-Hydroxyethyl)-31-hydroxy-20,30-oxa,29,30,31,32-tetrahydronodulisporamide;

Methyl 29,30,31,32-tetrahydronodulisporate;

1-Hydroxy-nodulisporic acid, methyl ester;

1-Hydroxy-32-descarboxy-32-hydroxymethyl-nodulisporic acid;

32-Descarboxy-32-isocyanato-nodulisporic acid;

32-Descarboxy-32-(1-carbomethoxyamino)-nodulisporic acid;

32-Descarboxy-32-(1-(3-benzyl)urea)-nodulisporic acid

32-Descarboxy-32-(1-(3-diethyloxy)urea)nodulisporic acid;

32-Descarboxy-32-(1-(3-(4-methoxybenzyl))urea)-nodulisporic acid;

32-Descarboxy-32-(1-(3-(2-propyl))urea)-nodulisporic acid;

32-Descarboxy-32-(1-(3-(5-aminopentyl))urea)-nodulisporic acid;

32-Descarboxy-32-(1-(3-(2-hydroxyethyl))urea)-nodulisporic acid;

32-Descarboxy-32-(1-(3-(3-dimethylaminopropyl))urea) nodulisporic acid;

32-Descarboxy-32-(1-(3-(3-morpholinopropyl))urea)nodulisporic acid;

32-Descarboxy-32-(1-(3-(2-pyridylmethyl))urea)nodulisporic acid; 32-Descarboxy-32-(1-(3-(2-piperazinoethyl))urea)nodulisporic acid;

31,32-Dihydro-31,32-dihydroxy-nodulisporic acid;

4,20-bis-O-acetyl-nodulisporic acid;

1-Hydroxy-nodulisporic acid;

29,30-Dihydro-nodulisporic acid;

1-Hydroxy-1-methyl-nodulisporic acid; and

1-Hydroxy-1-methyl-nodulipsoric acid, methyl ester.

* * * * *